(12) United States Patent
Sugahara et al.

(10) Patent No.: US 8,124,122 B2
(45) Date of Patent: Feb. 28, 2012

(54) FEMALE HORMONE-CONTAINING PATCH

(75) Inventors: Takaya Sugahara, Sanuki (JP);
Sadanobu Shirai, Takamatsu (JP);
Masahiro Yamaji, Higashikagawa (JP)

(73) Assignee: Teikoku Seiyaku Co., Ltd., Osaka (JP)

( * ) Notice: Subject to any disclaimer, the term of this patent is extended or adjusted under 35 U.S.C. 154(b) by 674 days.

(21) Appl. No.: 10/524,065

(22) PCT Filed: Aug. 7, 2003

(86) PCT No.: PCT/JP03/10030
§ 371 (c)(1),
(2), (4) Date: Feb. 8, 2005

(87) PCT Pub. No.: WO2004/014395
PCT Pub. Date: Feb. 19, 2004

(65) Prior Publication Data
US 2006/0127464 A1    Jun. 15, 2006

(30) Foreign Application Priority Data

Aug. 9, 2002  (JP) ................. 2002-233469
Aug. 9, 2002  (JP) ................. 2002-233470

(51) Int. Cl.
*A61F 13/00* (2006.01)
*A61F 13/02* (2006.01)

(52) U.S. Cl. ..................... 424/449; 424/448

(58) Field of Classification Search ............. 424/448, 424/449
See application file for complete search history.

(56) References Cited

U.S. PATENT DOCUMENTS

| 4,573,996 | A | * | 3/1986 | Kwiatek et al. ........... 424/434 |
| 5,242,951 | A | * | 9/1993 | Akemi et al. ............. 514/772.5 |
| 5,393,529 | A | * | 2/1995 | Hoffmann et al. ......... 424/445 |
| 5,693,335 | A | * | 12/1997 | Xia et al. ................. 424/448 |
| 5,820,877 | A | * | 10/1998 | Yamaguchi et al. ....... 424/449 |
| 5,876,745 | A | * | 3/1999 | Muraoka et al. .......... 424/448 |
| 6,177,098 | B1 | * | 1/2001 | Kawaji et al. ............ 424/443 |
| 2004/0091521 | A1 | * | 5/2004 | Radloff et al. ........... 424/449 |

FOREIGN PATENT DOCUMENTS

| EP | 0 435 200 A2 | 7/1991 |
| EP | 0 531 938 A1 | 3/1993 |
| EP | 0 737 477 A1 | 10/1996 |
| JP | SHO 60-152413 | 8/1985 |
| JP | SHO 61-155321 | 7/1986 |
| JP | HEI 6-51623 | 10/1988 |
| JP | HEI 3-44327 | 2/1991 |
| JP | HEI 4-342532 | 11/1992 |
| JP | HEI 5-148145 | 6/1993 |
| JP | 07-010759 | 1/1995 |
| JP | HEI 7-501335 | 2/1995 |
| JP | 07-101864 | 4/1995 |
| JP | HEI 9-503217 | 3/1997 |
| JP | HEI 9-505554 | 6/1997 |
| JP | 09-176049 | 7/1997 |
| JP | 09-315957 | 12/1997 |
| JP | 2000-063267 | 2/2000 |
| JP | 2000-119195 | 4/2000 |
| WO | WO 90/06736 A1 | 6/1990 |
| WO | WO 91/17752 A1 | 11/1991 |
| WO | WO 97/03698 A1 | 7/1996 |
| WO | WO 00/25792 A1 | 5/2000 |
| WO | WO 00/38659 A1 | 7/2000 |
| WO | WO 02/38134 A2 * | 5/2002 |

* cited by examiner

*Primary Examiner* — Anand Desai
*Assistant Examiner* — Melissa Mercier
(74) *Attorney, Agent, or Firm* — Ostrager Chong Flaherty & Broitman P.C.

(57) ABSTRACT

Provided herein is a female hormone-containing patch wherein an active ingredient is highly soluble in a pressure-sensitive adhesive layer and the active ingredient is not adsorbed to a backing, and the patch per se can follow the irregularities on the skin surface or body movements. The patch is an external patch containing, as a female hormone, a follicular hormone estradiol and/or its derivative or a progestational hormone norethisterone and/or its derivative. The external patch comprises an acrylic pressure-sensitive adhesive containing 0.01 to 1% by weight of an isocyanate-based crosslinking agent as an essential ingredient.

8 Claims, 8 Drawing Sheets

FEMALE HORMONE-CONTAINING PATCH

TECHNICAL FIELD

The present invention relates to an external patch containing a female hormone useful for prevention or treatment of diseases such as menopausal syndrome (e.g., headaches, hot flushes, sweating, etc.) which often occurs in climacteric or menopausal women, osteoporosis, Alzheimer's disease, arteriosclerosis, and hyperlipemia. Particularly, the present invention relates to an external patch containing, as a female hormone, a follicular hormone estradiol and/or its derivative or a progestational hormone norethisterone and/or its derivative.

BACKGROUND ART

In recent years, hormone replacement therapy is becoming established as an important method for preventing or treating diseases such as menopausal syndrome (e.g., headaches, hot flushes, sweating, etc.) which often occurs in climacteric or menopausal women, osteoporosis, Alzheimer's disease, arteriosclerosis, and hyperlipemia or for improving the QOL of middle-aged and older women.

In order to prevent, treat, or improve such diseases, a hormone drug is orally administered or injected in most cases. However, it is known that in the case where a female hormone such as a follicular hormone estrogen or a progestational hormone norethisterone is orally administered, the female hormone is absorbed from the alimentary canal and is then rapidly metabolized in the liver. Likewise, it is known that such a female hormone administered by injection is also rapidly metabolized in the liver. Therefore, in either case, the rate of utilization of the drug is significantly low.

Further, there is a possibility that not only impaired liver function but also side effects such as gallbladder disorder and uterine cancer are produced due to a high metabolic rate in the liver. Therefore, it is necessary to keep the drug concentration (i.e., a hormone administered) in the body at a minimum. For this reason, methods for administering a female hormone without allowing the female hormone to pass through the alimentary canal or the liver are being investigated. Among such methods, attention is particularly being given to transdermal absorption preparations from the viewpoint of excellent sustainability in drug release and handleability, and some preparations have already been studied.

For example, Japanese Patent Publication No. Hei 6-51623 discloses a reservoir-type transdermal absorption preparation in which estradiol and norethisterone acetate are dissolved in a gel made of hydroxypropyl cellulose and ethanol. This reservoir-type transdermal absorption preparation controls the release of estradiol and norethisterone acetate by the use of an ethylene-vinyl acetate film. Further, Japanese Patent Laid-Open Publication No. Sho 60-152413 discloses, for example, a transdermal absorption preparation of conjugated estrogens. This transdermal absorption preparation contains menthol as a transdermal absorption promoting agent. However, since these preparations contain a volatile ingredient, there is a fear that drug release characteristics may be changed. In addition, the preparation disclosed in Japanese Patent Publication No. Hei 6-51623 involves the risk of causing skin troubles such as rubor because ethanol contained therein is an irritant to the skin.

Further, International Publication No. WO 91/17752, Japanese Patent Laid-Open Publication No. Hei 5-148145, and Japanese Patent Laid-Open Publication No. 2000-119195 disclose patches manufactured using rubber pressure-sensitive adhesives such as a styrene-isoprene-styrene block copolymer. Furthermore, Japanese Patent Laid-Open Publication No. Sho 61-155321 discloses a patch including, as a main ingredient, an adhesive base material containing an adhesive resin material (e.g., polyterpene resin, hydrocarbon resins), natural rubber or synthetic rubber (e.g., polyisobutylene, styrene-butylene polymer, styrene-isoprene polymer, styrene-ethylene-butylene polymer, 1,4-polyisoprene) and a polymer capable of swelling in water, such as galactomannan. However, since these patches are manufactured using natural rubber or synthetic rubber as a pressure-sensitive adhesive, they are not suitable for prolonged skin application from the viewpoint of the characteristics of natural rubber or synthetic rubber.

In order to solve such a problem, preparations manufactured using acrylic pressure-sensitive adhesives enabling prolonged application are being investigated. As for estradiol, for example, Japanese Patent Laid-Open Publication No. Hei 3-44327, Translated National Publication of Patent Application No. Hei 7-501335, Translated National Publication of Patent Application No. Hei 9-503217, and Translated National Publication of Patent Application No. Hei 9-505554 disclose preparations manufactured using acrylic pressure-sensitive adhesives. Each of the preparations contains its own solvent and absorption accelerator agent to improve the transdermal absorbability of estradiol. However, these preparations are still not perform sufficient transdermal absorption for practical use, because they do not perform enough drug release depending on a solvent and an absorption accelerator agent or some of them are irritants to the skin and they have the risk of causing skin troubles such as rubor as a result of prolonged application.

It is generally difficult to allow an effective amount of drug to permeate through the skin because the skin tissue of a living body basically has a defense function to prevent the entrance of foreign substances into the living body. In order to solve such a problem, an absorption accelerator agent may be added. However, addition of an absorption promoting agent tends to increase the degree of skin irritation in most cases.

As for norethisterone, for example, Japanese Patent Laid-Open Publication No. Hei 4-342532 discloses a patch manufactured using an acrylic pressure-sensitive adhesive comprising 2-ethylhexyl acrylate and N-vinyl-2-pyrrolidone. However, since this preparation contains N-vinyl-2-pyrrolidone in a high concentration, norethisterone as a basis is dissolved in the pressure-sensitive adhesive, thus resulting in poor releasability of norethisterone from the preparation. In addition, this preparation has a problem in that it causes strong physical irritation to the skin due to its excessive adhesive strength. Therefore, the preparation cannot be used for prolonged and continuous administration.

Moreover, in the case where an external preparation is administered in hormone replacement therapy, it is necessary to apply the external preparation for a long period of time to maintain an effective blood level of a drug. In order to apply the external preparation for a long period of time, it is necessary to improve the adhesive strength of a base material of the external preparation. In addition, it is particularly necessary to enhance the anchor effect of a pressure-sensitive adhesive on the irregularities of the skin surface in order to increase a holding power. The anchor effect of a pressure-sensitive adhesive on the irregularities of the skin surface can be enhanced by increasing the activity of a polymer compound as an adhesive base material. However, by doing so, there is a possibility that the cohesive strength of the polymer compound is lowered so that cohesion failure occurs, thus resulting in the remaining of the pressure-sensitive adhesive on the skin after peeling-off of the external preparation. Therefore, it is necessary to control the anchor effect of the pressure-sensitive adhesive and the cohesive strength of the pressure-sensitive adhesive to allow the external preparation'to be applied for a long period of time.

In many articles, it has already become apparent that the flexibility of a backing of an external patch has a strong bearing on an increase of the transdermal drug absorption. Examples of a backing having physical properties adequate for this purpose include low-density polymer films, non-woven fabrics, and woven fabrics. It is necessary for them to have a free volume sufficient to obtain flexibility. However, when the free volume of the backing is too large, there is a problem in that drug releasability is lowered after the external patch is stored for a long period of time due to the adsorption of a drug to the backing layer, so that such an external patch cannot deliver satisfactory performance.

DISCLOSURE OF THE INVENTION

In view of the above fact, it is therefore an object of the present invention to provide an external patch containing a female hormone and satisfying the following points (1) to (4):
(1) having improved drug releasability per unit area;
(2) having a low degree of skin irritation;
(3) having an improved adhesive strength enough to withstand prolonged application while preventing cohesive failure from occurring when the external patch is peeled off after the completion of prolonged application; and
(4) having a flexible backing enabling the transdermal absorbability of a drug to be improved without the drug being adsorbed to the backing.

Specifically, it is an object of the present invention to provide an external patch containing, as a female hormone, a follicular hormone estradiol and/or its derivative or a progestational hormone norethisterone and/or its derivative.

In order to achieve the above object, the present inventors have intensively investigated, and as a result, they have found that by using an acrylic pressure-sensitive adhesive containing, as an essential ingredient, 0.01 to 1% by weight of an isocyanate-based crosslinking agent to form an acrylic pressure-sensitive adhesive layer and allowing 0.5 to 10% by weight of a female hormone as an active ingredient to be contained in the acrylic pressure-sensitive adhesive layer, it is possible to obtain a favorable external patch.

Further, they have also found, in the case where a female hormone to be contained in the external patch is a follicular hormone estradiol and/or its derivative, that crotamiton and oleic acid are effective in controlling the distribution or diffusion of estradiol and/or its derivative to or in the skin, that crotamiton and oleic acid are preferably contained in the acrylic pressure-sensitive adhesive layer at optimum ratios, thereby reducing skin irritation, and that a laminate structure comprising a polyethylene terephthalate film and a flexible polymer film, a non-woven fabric, or a woven fabric can be effectively used as a backing.

Furthermore, they have also found, in the case where a female hormone to be contained in the external patch is a progestational hormone norethisterone and/or its derivative, that a distribution coefficient between the preparation and the skin is an important factor, that isopropyl myristate is effective in controlling the distribution coefficient of norethisterone contained in the acrylic pressure-sensitive adhesive, and that isopropyl myristate is preferably contained in the acrylic pressure-sensitive adhesive layer at an optimum ratio, thereby reducing skin irritation. These findings have led to the completion of the present invention.

According to a first aspect of the present invention based on the basic concept provided by the invention, there is provided an estradiol (follicular hormone)-containing external patch comprising a backing and a pressure-sensitive adhesive layer, wherein the pressure-sensitive adhesive layer is made of an acrylic pressure-sensitive adhesive containing 0.01 to 1% by weight of an isocyanate-based crosslinking agent as an essential ingredient and contains 0.5 to 10% by weight of estradiol and/or its derivative as an active ingredient, 0.1 to 10% by weight of crotamiton, and 0.1 to 10% by weight of oleic acid.

That is, the first aspect of the present invention is characterized in that a pressure-sensitive adhesive layer is made of an acrylic pressure-sensitive adhesive containing 0.01 to 1% by weight of an isocyanate-based crosslinking agent as an essential ingredient and contains estradiol and/or its derivative as an active ingredient, and further contains oleic acid and crotamiton at specific ratios.

According to a second aspect of the present invention based on the basic concept provided by the invention, there is provided a norethisterone (progestational hormone)-containing external patch comprising a backing and a pressure-sensitive adhesive layer, wherein the pressure-sensitive adhesive layer is made of an acrylic pressure-sensitive adhesive containing 0.01 to 1% by weight of an isocyanate-based crosslinking agent as an essential ingredient and contains 1 to 30% by weight of isopropyl myristate as a distribution coefficient control agent and 0.5 to 10% by weight of norethisterone and/or its derivative as an active ingredient.

That is, the second aspect of the present invention is characterized in that a pressure-sensitive adhesive layer is made of an acrylic pressure-sensitive adhesive containing 0.01 to 1% by weight of an isocyanate-based crosslinking agent as an essential ingredient and a specific amount of isopropyl myristate as a distribution coefficient control agent is contained in the acrylic pressure-sensitive adhesive, thereby improving the transdermal absorbability of an active ingredient contained in the pressure-sensitive adhesive layer and reducing skin irritation.

In the external patches of the first and second aspects of the present invention, it is more preferred that the backing be a laminate structure comprising a polyethylene terephthalate film having a thickness of 0.1 to 10 μm and a flexible polymer film, a non-woven fabric, or a woven fabric having a thickness of 1 to 200 μm.

By using such a backing, it is possible to prevent estradiol and/or its derivative or norethisterone and/or its derivative as an active ingredient of the external patch from being adsorbed to the backing, and as a result, the active ingredient is very effectively released.

DESCRIPTION OF THE SYMBOLS IN THE DRAWINGS

A: backing
1: flexible film
2: drug non-adsorptive layer
3: pressure-sensitive adhesive layer
4: release liner
5: patch
6: water
7: glass plate
8: stirrer

BEST MODE FOR CARRYING OUT THE INVENTION

Hereinbelow, the present invention will be described in detail.

As adhesive base materials used in manufacturing an external patch, natural rubber, synthetic rubber pressure-sensitive adhesives, acrylic pressure-sensitive adhesives, and silicon pressure-sensitive adhesives are generally known. The present inventors have found that in the case where natural rubber or a synthetic rubber pressure-sensitive adhesive is used as an adhesive base material of an external patch, the releasability of a female hormone as an active ingredient contained in a pressure-sensitive adhesive layer is lowered due to a strong interaction between the natural rubber or the synthetic rubber pressure-sensitive adhesive and the female hormone.

In addition, since natural rubber and synthetic rubber pressure-sensitive adhesives are inherently hydrophobic, they are not resistant to sweat and water. Therefore, in hot and humid surroundings or during taking a bath or exercise, there is a possibility that sweat or water enters between the pressure-sensitive adhesive layer and the skin, thus resulting in a reduction in the migration of a drug to the skin or separation of the external patch from the skin. From the fact, it can be said that such an external patch manufactured using natural rubber or a synthetic rubber pressure-sensitive adhesive as an adhesive base material is not suitable for. prolonged application that is one of the requirements of a preparation of the present invention.

Further, in the case where a silicon pressure-sensitive adhesive is used as an adhesive base material, final material composition becomes specific. Since this becomes a factor of an increase in cost, a silicon pressure-sensitive adhesive is not preferable. As a result of investigation, the present inventors have found that an acrylic pressure-sensitive adhesive is most preferable as an adhesive base material for use in manufacturing the external patch of the present invention containing a female hormone as an active ingredient.

Examples of a monomer constituting the acrylic pressure-sensitive adhesive include acrylic acid, vinyl acetate, and acrylic esters such as ethyl acrylate and 2-ethylhexyl acrylate.

The amount of each of the monomer components to be mixed is appropriately determined according to, for example, desired physical properties of an acrylic pressure-sensitive adhesive to be obtained, but 2-ethylhexyl acrylate is preferably contained in an amount of 5 to 50% by weight, acrylic acid is preferably contained in an amount of 1 to 10% by weight, ethyl acrylate is preferably contained in an amount of 5 to 50% by weight, and vinyl acetate is preferably contained in an amount of 5 to 50% by weight.

In the meantime, in hormone replacement therapy, it is necessary to maintain or sustain an effective blood level of an active ingredient. Therefore, administration of an external preparation requires that a patch should be applied for a long period of time. Improvement in the adhesive strength of a patch, in particular, improvement in the holding power of an external patch requires enhancement of the anchor effect of a pressure-sensitive adhesive on the irregularities of the skin surface. In order to enhance such an anchor effect, it is necessary to increase the creep of a polymer compound as an adhesive base material. However, by doing so, there is a possibility that the cohesive strength of the polymer compound is decreased so that cohesive failure occurs when the external patch is peeled off, thus resulting in the remaining of the pressure-sensitive adhesive on the skin after peeling-off of the external patch. For this reason, it is necessary to control the anchor effect and the cohesive strength of the pressure-sensitive adhesive.

In view of such a problem, the present inventors have made an intensive study, and as a result, they have found that by loosely crosslinking a polymer compound component as an adhesive base material by the use of a small amount of crosslinking agent, it is possible to allow the adhesive base material to exert an effective anchor effect on the skin while preventing the occurrence of cohesive failure when an external patch is peeled off.

Such a crosslinking agent is not limited to any specific one as long as it can effectively crosslink an acrylic pressure-sensitive adhesive. It has been found that, among such crosslinking agents, an isocyanate-based crosslinking agent is most preferable. The amount of the crosslinking agent to be mixed is in the range of 0.01 to 1% by weight, preferably in the range of 0.1 to 0.7% by weight. If the amount of the crosslinking agent to be mixed is less than 0.01% by weight, the occurrence of cohesive failure is not effectively prevented. On the other hand, if the amount of the crosslinking agent to be mixed exceeds 1% by weight, the creep of the polymer compound component as an adhesive base material is decreased so that an effective anchor effect cannot be obtained.

The external patch of the present invention is manufactured by using such an acrylic pressure-sensitive adhesive as a base material and allowing a female hormone as an active ingredient to be contained in the acrylic pressure-sensitive adhesive.

Hereinbelow, each of the aspect of the external patch of the present invention will be explained individually.

The first aspect of the present invention is characterized in that the above-mentioned pressure-sensitive adhesive layer is made of an acrylic pressure-sensitive adhesive containing 0.01 to 1% by weight of an isocyanate-based crosslinking agent as an essential ingredient, contains 0.5 to 10% by weight of estradiol and/or its derivative as an active ingredient, and further contains oleic acid and crotamiton at specific ratios.

In this case, the amount of estradiol and/or its derivative to be mixed is not particularly limited and varies depending on a pressure-sensitive adhesive component to be used and the amount of oleic acid and crotamiton to be mixed (which will be described later), but is preferably in the range of 0.5 to 10% by weight. If the amount of estradiol and/or its derivative to be mixed is less than 0.5% by weight, the level of estradiol and/or its derivative in the blood does not become sufficient. On the other hand, even if the amount of estradiol and/or its derivative to be mixed exceeds 10% by weight, an increase in the mixing ratio thereof does not proportionately increase the level of estradiol and/or its derivative in the blood. In addition, there is an undesired possibility that estradiol and/or its derivative is crystallized in the pressure-sensitive adhesive.

Crotamiton imparts high solubility to estradiol and/or its derivative as an active ingredient to prevent the crystallization of estradiol and/or its derivative in the pressure-sensitive adhesive layer. Further, crotamiton increases the concentration of a drug being in solution and having a good diffusion activity, and controls the distribution of the drug to the skin according to a relative concentration to estradiol.

The amount of crotamiton to be mixed is in the range of 0.1 to 10% by weight, preferably in the range of 0.5 to 5% by weight. If the amount of crotamiton to be mixed is less than 0.1% by weight, the above effects cannot be obtained. On the other hand, if the amount of crotamiton to be mixed exceeds 10% by weight, the solubility of estradiol contained in the preparation is excessively increased so that the distribution of estradiol to the skin is reduced. In addition, there is an undesired possibility that skin irritation occurs due to excessive crotamiton.

Oleic acid is used together with crotamiton. Oleic acid breaks the structure of lipid membrane of corneous cells having the greatest skin's defense function, that is, a barrier function to increase the diffusion coefficient of estradiol in the skin. In this way, oleic acid exerts an absorption promoting effect.

The amount of oleic acid to be mixed varies depending on the amount of crotamiton to be mixed together with oleic acid, but is in the range of 0.1 to 10% by weight, preferably in the range of 0.5 to 5% by weight.

If the amount of oleic acid to be mixed is less than 0.1% by weight, such an absorption promoting effect cannot be obtained. On the other hand, even if the amount of oleic acid to be mixed exceeds 10% by weight, an increase in the amount of oleic acid to be mixed does not proportionately enhance the absorption promoting effect.

The second aspect of the present invention is characterized in that a pressure-sensitive adhesive layer is made of an acrylic pressure-sensitive adhesive containing 0.01 to 1% by weight of an isocyanate-based crosslinking agent as an essential ingredient and contains 1 to 30% by weight of isopropyl myristate as an essential ingredient and norethisterone and/or its derivative as an active ingredient.

Norethisterone and/or its derivative has a high degree of solubility in the acrylic pressure-sensitive adhesive, which leads to poor releasability of a drug from the pressure-sensitive adhesive. However, by allowing isopropyl myristate to be contained in the adhesive base material, it becomes possible to control the distribution of norethisterone to the adhesive base material, thereby improving the releasability of the drug.

The amount of an active ingredient norethisterone and/or its derivative to be mixed is not particularly limited and varies depending on a pressure-sensitive adhesive component to be used, the amount of isopropyl myristate to be mixed, and the structure of a backing to be used (which will be described later), but is in the range of 0.5 to 10% by weight, preferably in the range of 1 to 7% by weight, more preferably in the range of 3.0 to 5% by weight. If the amount of norethisterone and/or its derivative to be mixed is less than 0.5% by weight, the level of norethisterone and/or its derivative in the blood does not become sufficient. On the other hand, even if the amount of norethisterone and/or its derivative to be mixed exceeds 10% by weight, an increase in the mixing ratio thereof does not proportionately increase the level of norethisterone and/or its derivative in the blood. In addition, there is an undesired possibility that norethisterone and/or its derivative is crystallized in the pressure-sensitive adhesive.

The amount of isopropyl myristate to be mixed is in the range of 1 to 30% by weight, preferably in the range of 3 to 20% by weight, more preferably in the range of 5 to 10% by weight. If the amount of isopropyl myristate to be mixed is less than 1% by weight, the above effect cannot be obtained. On the other hand, if the amount of isopropyl myristate to be mixed exceeds 30% by weight, it becomes difficult to maintain the cohesive strength of the pressure-sensitive adhesive even when an excessive amount of crosslinking agent is mixed, thereby, for example, causing a problem in that the pressure-sensitive adhesive remains on the skin surface after the external patch is peeled off.

In the meantime, it has been already apparent that the flexibility of the backing of an external patch strongly contribute to the improvement of the transdermal absorbability of an active ingredient contained in a pressure-sensitive adhesive layer. Examples of a backing having physical properties adequate for such a purpose include low-density polymer films, non-woven fabrics, and woven fabrics. In the case where they are used singly as a backing, it is necessary for them to have a sufficient volume to obtain flexibility. Therefore, an external patch manufactured in such a manner involves a problem in that drug releasability is lowered after the external patch is stored for a long period of time due to the occurrence of adsorption of a drug to the backing, so that the external patch may not be satisfactory. In the case of the external patch of the present invention containing a female hormone as an active ingredient, it is necessary to avoid lowering of drug releasability as far as possible.

In view of such a problem, the present inventors have made investigation of a backing suitable for an external patch containing a female hormone as an active ingredient. As a result, it has been confirmed that the use of a laminate structure comprising a drug non-adsorptive layer having a very thin and dense structure and a flexible film capable of following the irregularities on the skin or body movements as a backing makes it possible to prevent the adsorption of the active ingredient to the backing, thereby improving the transdermal absorbability of a drug.

Figure 1:
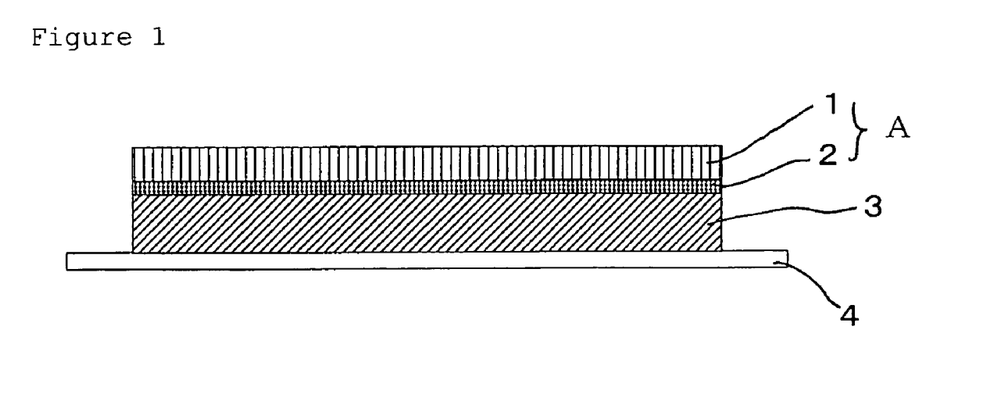
FIG. 1 is a cross-sectional view of an external patch of the present invention.

FIG. 1 shows the structure of such a backing. As shown in FIG. 1, a backing A to be used for the external patch of the present invention is a laminate structure comprising a flexible film 1 and a drug non-adsorptive layer 2 having a thin and dense structure. The external patch of the present invention has a structure in which a pressure-sensitive adhesive layer 3 containing an active ingredient is laminated on the drug non-adsorptive layer 2 and a release liner 4 is laminated on the pressure-sensitive adhesive layer 3.

As described above, the backing A to be used for the external patch of the present invention is characterized in that the drug non-adsorptive layer 2 having a thin and dense structure is provided on the pressure-sensitive adhesive layer to prevent the adsorption of an active ingredient to the backing and the flexible film 1 is provided to allow the external patch to follow the irregularities on the skin or body movements.

The drug non-adsorptive layer is not limited to any specific one as long as it has a dense structure, can be formed into a thin film, and does not interact with the components of the pressure-sensitive adhesive layer, such as an active ingredient. Examples of such a drug non-adsorptive layer include metal films, evaporated metals, and high-density polymer films (polyethylene terephthalate film). Among them, a polyethylene terephthalate film is preferable from the viewpoint of versatility and manufacturing costs. The thickness of the drug non-adsorptive layer e.g., a polyethylene terephthalate film is preferably in the range of about 0.1 to 20 μm. If the thickness of the polyethylene terephthalate film exceeds 20 μm, the external patch cannot follow the irregularities on the skin or body movements due to the stiffness of the polyethylene terephthalate film, and therefore the transdermal absorbability of an active ingredient contained in the pressure-sensitive adhesive layer is lowered.

On the other hand, the flexible film to be laminated on the drug non-adsorptive layer is not limited to any specific one as long as it can follow the irregularities on the skin or body movements. Examples of such a flexible film include woven fabrics, non-woven fabrics, and polymer films made of polyethylene, polypropylene, polyurea, polyurethane, polyester, polyvinyl alcohol, polyvinyl chloride, or polymeric elastomers. The thickness of the film is in the range of about 1 to 200 μm, preferably in the range of about 2 to 100 μm, more preferably in the range of about 5 to 50 μm.

If the thickness of the flexible film layer is less than 1 μm, it is difficult to apply a preparation to the skin because the preparation is bent or warped when the release liner is removed due to the lack of elasticity. On the other hand, if the thickness of the flexible film layer exceeds 200 μm, it becomes difficult for a preparation to follow the irregularities on the skin surface or body movements so that the transdermal absorbability of an active ingredient is lowered.

The external patch according to the present invention can be manufactured, for example, in such a manner as described below. 39% by weight of 2-ethyihexyl acrylate, 1% by weight of acrylic acid, 40% by weight of ethyl acrylate, and 20% by weight of vinyl acetate are mixed, and are then subjected to polymerization for 24 hours at 60° C. under reduced pressure in ethyl acetate by the use of benzoyl peroxide as a polymerization initiator to obtain an ethyl acetate solution of an acrylic pressure-sensitive adhesive. A female hormone estradiol and/or its derivative or norethisterone and/or its derivative as an active ingredient and desired components are added to the acrylic pressure-sensitive adhesive solution and then stirred. The thus obtained mixture is applied on a release liner and dried, and then a backing is laminated thereon. The thus resultant product is cut into a desired size to obtain an external patch.

In the external patch of the present invention manufactured in such a manner, since a female hormone such as estradiol and/or its derivative or norethisterone and/or its derivative as an active ingredient contained in the pressure-sensitive adhesive layer is well dissolved in the pressure-sensitive adhesive layer, the active ingredient is not adsorbed to the backing. In addition, the external patch per se can follow the irregularities on the skin surface or body movements. Therefore, the external patch can provide an excellent transdermal absorbability of an active ingredient contained in the pressure-sensitive adhesive layer and can withstand prolonged application. Such an external patch is useful for prevention or treatment of diseases such as menopausal syndrome (e.g., headaches, hot flushes, sweating, etc.) which often occurs in climacteric or menopausal women, osteoporosis, Alzheimer's disease, arteriosclerosis, and hyperlipemia.

EXAMPLES

Hereinbelow, the present invention will be described in more detail with reference to Examples. Incidentally, the word "part" in the following Examples and Comparative Examples means "part by weight."

A: Estradiol-containing Patch

Examples 1 to 4

According to the manufacturing method described above and a formula shown in Table 1, estradiol-containing external patches of the present invention were obtained. Each of the estradiol-containing external patches of Examples 1 to 3 was manufactured by laminating a pressure-sensitive adhesive layer on a polyethylene terephthalate film constituting a backing (a laminate structure) having a predetermined thickness and cutting the thus obtained product into a desired size.

Note that the estradiol-containing external patch of Example 4 was manufactured by subjecting a low-density polyethylene film having a thickness of 50 μm as a backing to aluminum vapor deposition, laminating a pressure-sensitive adhesive layer on the aluminum-deposited surface of the low-density polyethylene film, and cutting the thus obtained product into a desired size.

TABLE 1

| Constituent (part) | Examples | | | |
| --- | --- | --- | --- | --- |
|  | 1 | 2 | 3 | 4 |
| Estradiol | 5.00 | 5.00 | 5.00 | 5.00 |
| Crotamiton | 2.50 | 2.50 | 2.50 | 2.50 |
| Oleic acid | 2.50 | 2.50 | 2.50 | 2.50 |
| Acrylic pressure-sensitive adhesive | 89.80 | 89.80 | 89.80 | 89.80 |
| Isocyanate-based crosslinking agent | 0.20 | 0.20 | 0.20 | 0.20 |
| Backing | Thickness (μm) | | | |
| Polyethylene terephthalate film | 3 | 5 | 10 | — |
| Low-density polyethylene film | 50 | 50 | 50 | — |
| Aluminum-evaporated low-density polyethylene film | — | — | — | 50 |

Comparative Examples 1 to 8

According to the manufacturing method described above and a formula shown in Table 2, estradiol-containing external patches of Comparative Examples 1 to 8 were obtained. Each of the estradiol-containing external patches of Comparative Examples 1 to 5 was manufactured by laminating a pressure-sensitive adhesive layer on a polyethylene terephthalate film constituting a backing having a predetermined thickness and cutting the thus obtained product into a desired size.

Note that Comparative Example 6 used a low-density polyethylene film having a thickness of 50 μm as a backing (a monolayer structure), Comparative Example 7 used a polyvinyl 15 chloride film having a thickness of 50 μm as a backing (a monolayer structure), and Comparative Example 8 used a polyurethane film having a thickness of 50 μm as a backing (a monolayer structure). Each of the estradiol-containing external patches of Comparative Examples 6 to 8 was manufactured by laminating a pressure-sensitive adhesive layer on the backing and cutting the thus obtained product into a desired size.

|  | Comparative Examples | | | | | | | |
|---|---|---|---|---|---|---|---|---|
| Constituent (part) | 1 | 2 | 3 | 4 | 5 | 6 | 7 | 8 |
| Estradiol | 5.0 | 5.0 | 5.0 | 5.0 | 5.0 | 5.0 | 5.0 | 5.0 |
| Crotamiton | — | 2.5 | — | 2.5 | 2.5 | 2.5 | 2.5 | 2.5 |
| Oleic acid | — | — | 2.5 | 2.5 | 2.5 | 2.5 | 2.5 | 2.5 |
| Acrylic pressure-sensitive adhesive | 94.8 | 92.3 | 92.3 | 89.8 | 89.8 | 89.8 | 89.8 | 89.8 |
| Isocyanate-based crosslinking agent | 0.2 | 0.2 | 0.2 | 0.2 | 0.2 | 0.2 | 0.2 | 0.2 |
| Backing | Thickness (μm) | | | | | | | |
| Polyethylene terephthalate film | 3 | 3 | 3 | 30 | 50 | — | — | — |
| Low-density polyethylene film | 50 | 50 | 50 | 50 | 50 | 50 | — | — |
| Polyvinyl chloride film | — | — | — | — | — | — | 50 | — |
| Polyurethane film | — | — | — | — | — | — | — | 50 |

Test Example 1

Measurement of Level of Estradiol in Blood of Rats (Part 1)

Four rats were used as one test group. The back region of each of the rats was shaved, and then the external patches of Example 1 and Comparative Examples 1, 2, and 3 each having a size of 9 cm² were applied to the back regions shaved of the rats, respectively. The blood of each of the rats was sampled with the lapse of time to measure the level of estradiol in the blood by RIA method. The measurement results are shown in FIG. 2.

Figure 2:
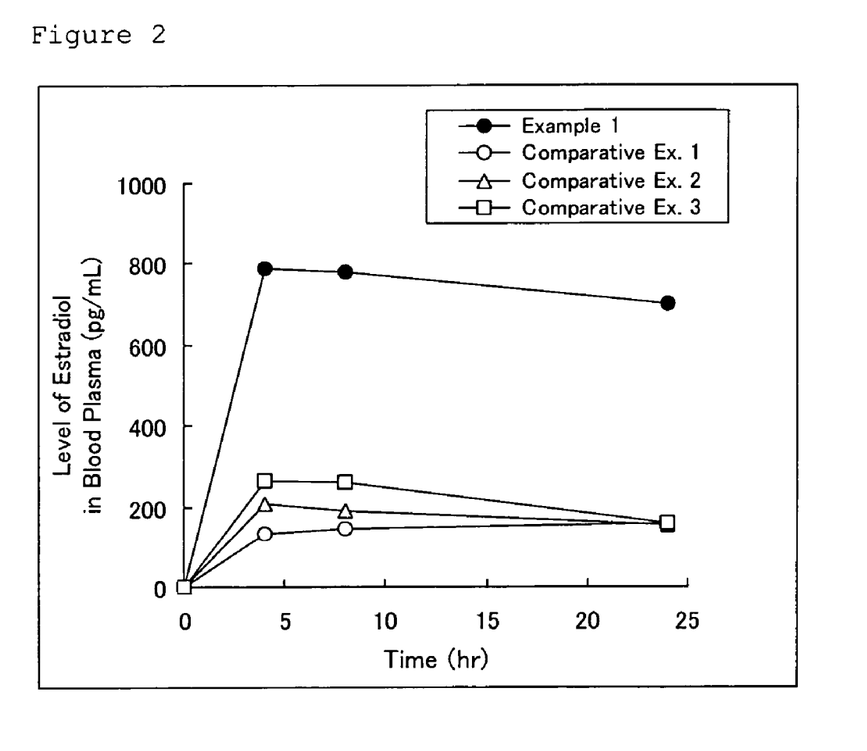
FIG. 2 is a graph, which shows the result of Test Example 1 in which the level of estradiol in the blood was measured in rats.

As is apparent from FIG. 2, in each of the cases of the external patch of Comparative Example 1 containing no oleic acid and crotamiton and the external patches of Comparative Examples 2 and 3 each containing either oleic acid or crotamiton, virtually no change was observed in the level of estradiol in the blood with the lapse of time. On the other hand, in the case of the external patch of Example 1 containing both of oleic acid and crotamiton, the level of estradiol in the blood became obviously high. From the results, it has been confirmed that the external patch of the present invention is useful.

Test Example 2

Measurement of Level of Estradiol in Blood of Rats (Part 2)

Figure 3:
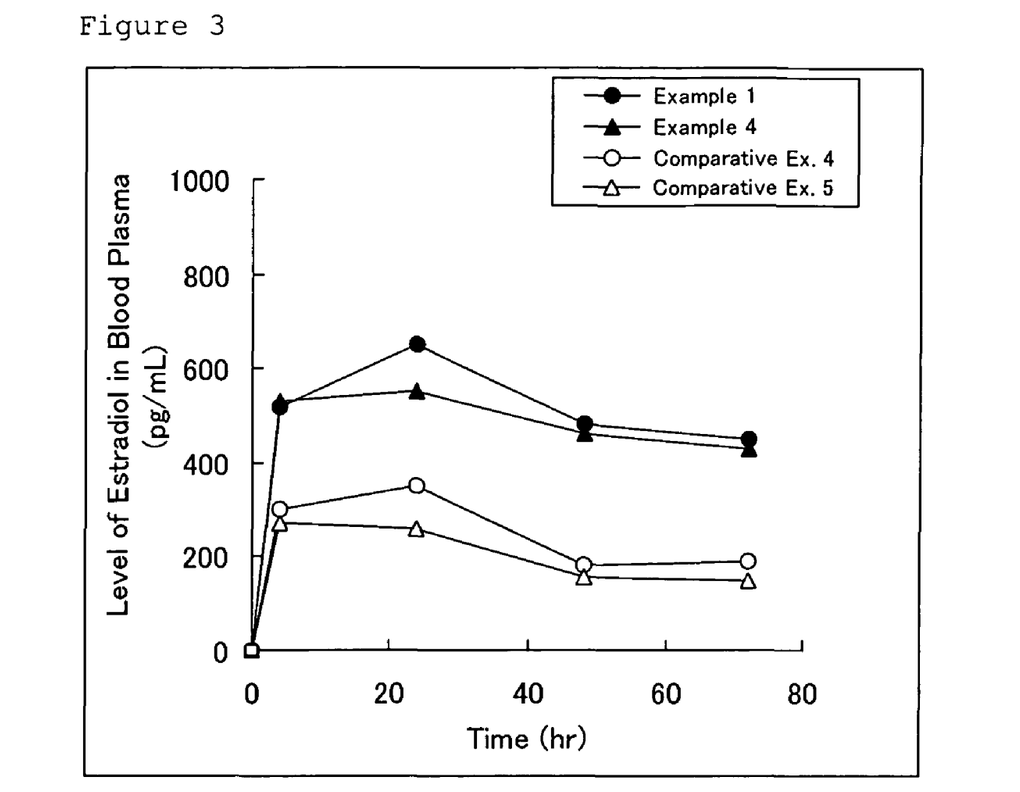
FIG. 3 is a graph, which shows the result of Test Example 2 in which the level of estradiol in the blood was measured in rats.

The back region of each of rats was shaved, and then the external patches of Examples 1 and 4 and Comparative Examples 4 and 5 each having a size of 9 cm² were applied to the back regions shaved of the rats, respectively. The blood of each of the rats was sampled with the lapse of time to measure the level of estradiol in the blood by RIA method. The measurement results are shown in FIG. 3. Incidentally, four rats were used as one test group.

As is apparent from FIG. 3, in the cases of the external patch of Example 1 of the present invention manufactured using, as a backing, a laminate structure comprising a thin polyethylene terephthalate film having a thickness of 3 μm and a low-density polyethylene film having a thickness of 50 μm and the external patch of Example 4 of the present invention manufactured using, as a backing, a low-density polyethylene film which had been subjected to aluminum vapor deposition, the level of estradiol in the blood remained at an obviously higher level by virtue of the flexibility of the backing as compared to the cases of the external patch of Comparative Example 4 manufactured using, as a backing, a laminate structure comprised of a polyethylene terephthalate film having a thickness of 30 μm and a low-density polyethylene film having a thickness of 50 μm and the external patch of Comparative Example 5 manufactured using, as a backing, a laminate structure comprised of a polyethylene terephthalate film having a thickness of 50 pm and a low-density polyethylene film having a thickness of 50 μm.

Test Example 3

Active Ingredient Release Test after Storage (Part 1)

Figure 4:
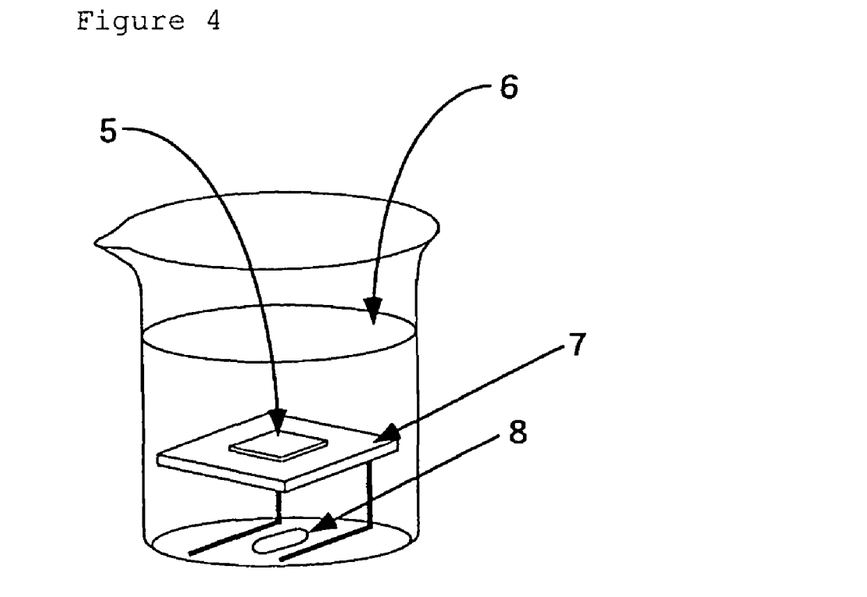
FIG. 4 is a schematic view of an apparatus for use in carrying out a release test in Test Example 3.
Figure 5:
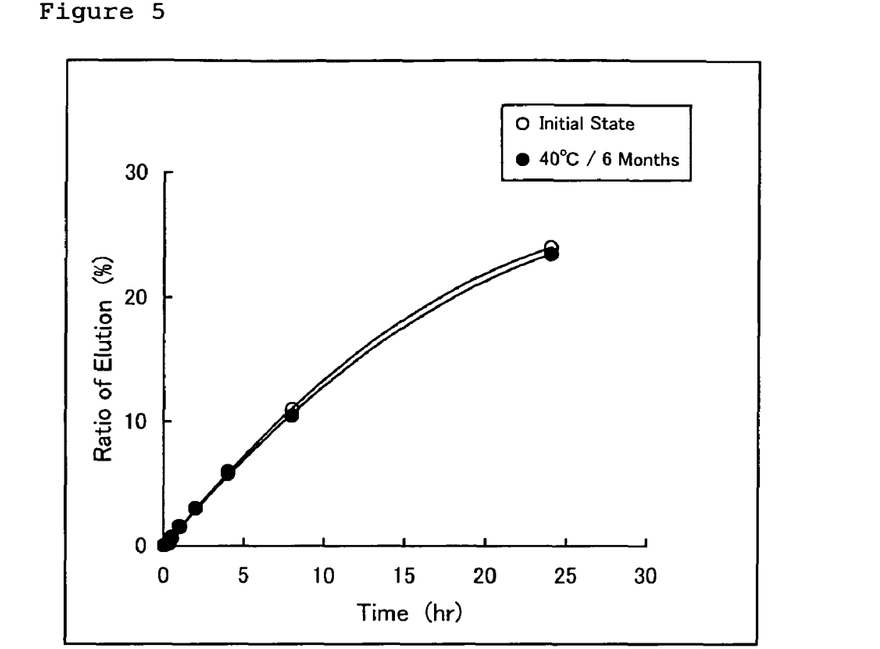
FIG. 5 is a graph, which shows the result of Test Example 3 carried out using an external patch of Example 1.
Figure 6:
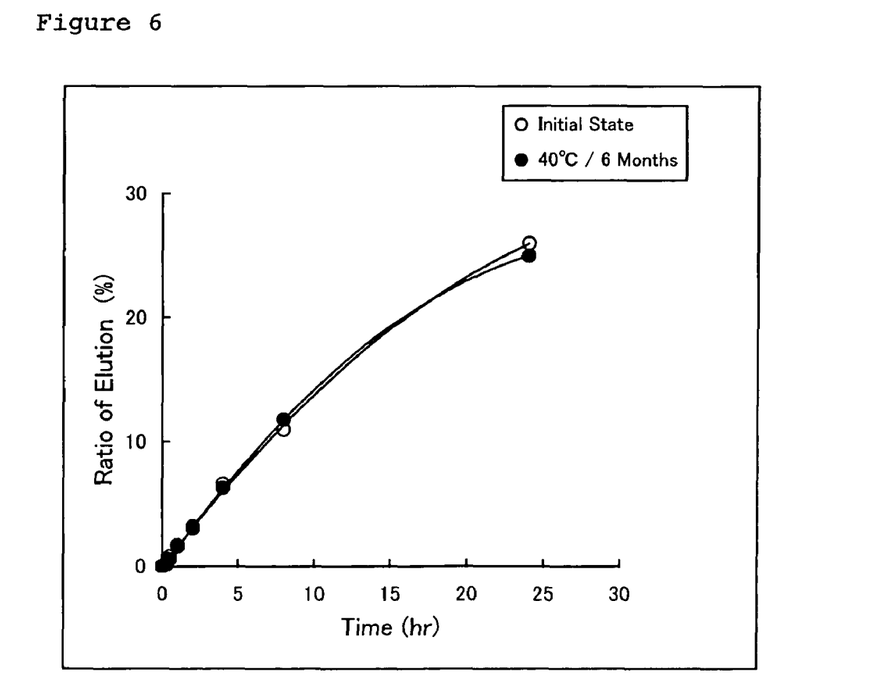
FIG. 6 is a graph, which shows the result of Test Example 3 carried out using an external patch of Example 4.
Figure 7:
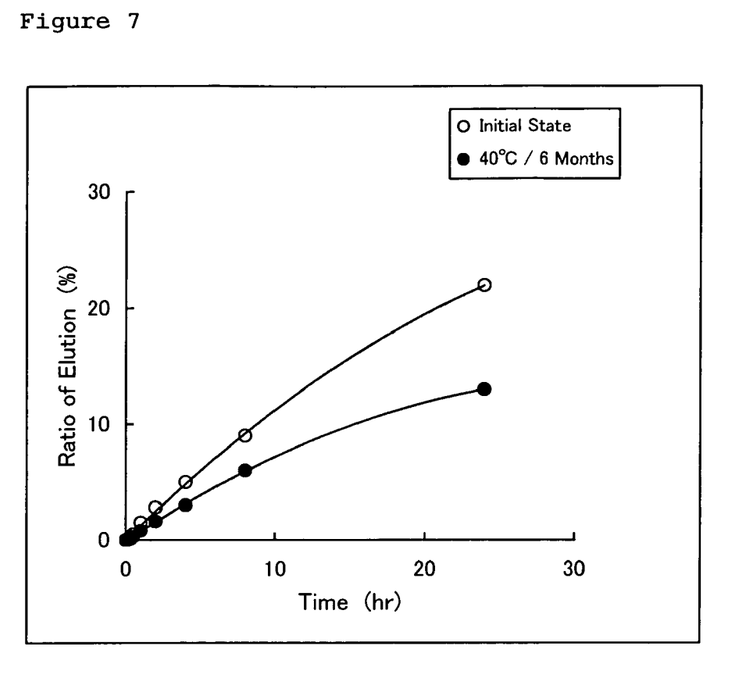
FIG. 7 is a graph, which shows the result of Test Example 3 carried out using an external patch of Comparative Example 6.
Figure 8:
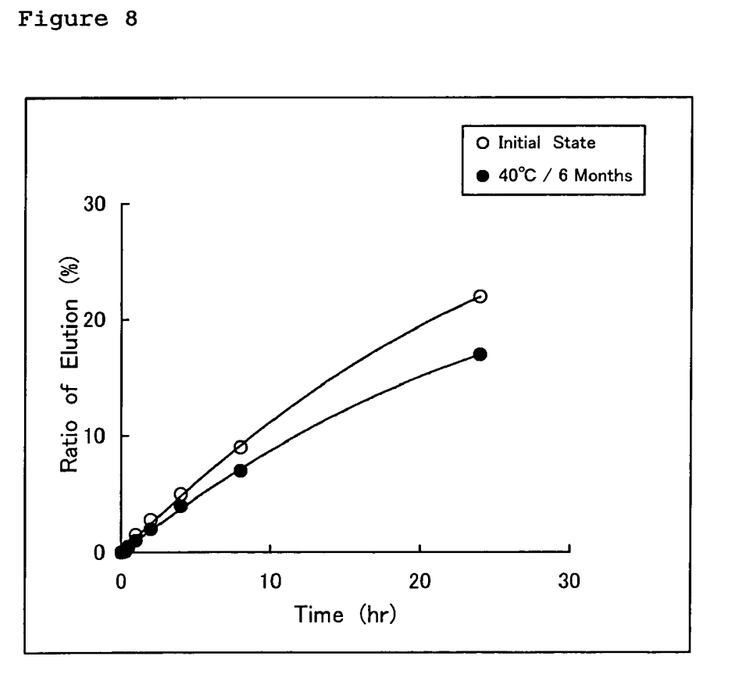
FIG. 8 is a graph, which shows the result of Test Example 3 carried out using an external patch of Comparative Example 7.
Figure 9:
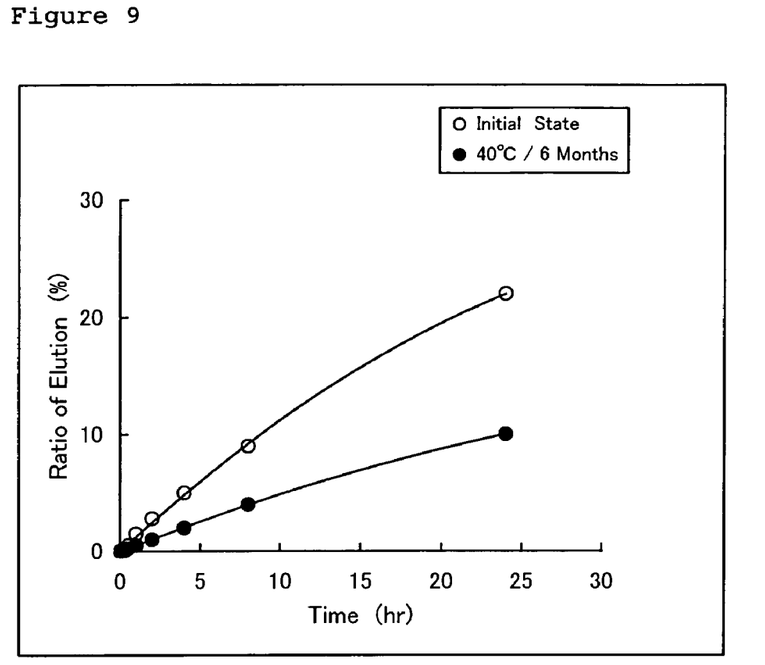
FIG. 9 is a graph, which shows the result of Test Example 3 carried out using an external patch of Comparative Example 8.

The external patches of Examples 1 and 4 and Comparative Examples 6, 7, and 8 were stored for 6 months at 40° C., and were then subjected to a release test according to a method shown in FIG. 4 to determine the adsorbability of estradiol to the backing. The adsorbability of estradiol to the backing was evaluated by comparing the releasability of estradiol between the external patch after 6-month storage and the external patch in the initial state after manufacturing. The results are shown in FIGS. 5, 6, 7, 8, and 9.

In each of the cases of the external patch manufactured using a low-density polyethylene film as a backing (Comparative Example 6, FIG. 7), the external patch manufactured using a polyvinyl chloride film as a backing (Comparative Example 7, FIG. 8), and the external patch manufactured using a polyurethane film as a backing (Comparative Example 8, FIG. 9), it can be concluded that the releasability of estradiol as an active ingredient was impaired due to the occurrence of adsorption of estradiol to the backing.

On the other hand, in each of the cases of the external patch of Example 1 manufactured using, as a backing, a laminate structure comprising a polyethylene terephthalate film and a low-density polyethylene film (FIG. 5) and the external patch of Example 4 manufactured using, as a backing, a polyethylene terephthalate film which had been subjected to aluminum vapor deposition (FIG. 6), the releasability of estradiol was not impaired even after the external patch was stored for 6 months at 40° C. From the result, it was confirmed that the adsorption of estradiol to the backing did not occur.

B: Norethisterone-containing Patch

Examples 5 to 7

According to the manufacturing method described above and a formula shown in Table 3, norethisterone acetate-containing external patches of the present invention were obtained. Each of the norethisterone acetate-containing external patches of Examples 5 to 7 was manufactured by laminating a pressure-sensitive adhesive layer on a polyethylene terephthalate film constituting a backing (a laminate structure) having a predetermined thickness and cutting the thus obtained product into a desired size.

TABLE 3

| | Examples | | |
|---|---|---|---|
| Constituent (part) | 5 | 6 | 7 |
| Norethisterone acetate | 5.00 | 5.00 | 5.00 |
| Isopropyl myristate | 5.00 | 10.00 | 20.00 |
| Acrylic pressure-sensitive adhesive | 89.80 | 84.80 | 74.80 |
| Isocyanate-based crosslinking agent | 0.20 | 0.20 | 0.20 |
| Backing | Thickness (μm) | | |
| Polyethylene terephthalate film | 3 | 3 | 3 |
| Low-density polyethylene film | 50 | 50 | 50 |

Comparative Examples 9 to 14

According to the manufacturing method described above and a formula shown in Table 4, norethisterone acetate-containing external patches of Comparative Examples 9 to 14 were obtained. Each of the norethisterone acetate-containing external patches of Comparative Examples 9 to 14 was manufactured by laminating a pressure-sensitive adhesive layer on a polyethylene terephthalate film constituting a backing having a predetermined thickness and cutting the thus obtained product into a desired size.

Note that Comparative Example 12 used a low-density polyethylene film having a thickness of 50 μm as a backing (a monolayer structure), Comparative Example 13 used a polyvinyl chloride film having a thickness of 50 μm as a backing (a monolayer structure), and Comparative Example 14 used a polyurethane film having a thickness of 50 μm as a backing (a monolayer structure). Each of the norethisterone acetate-containing external patches of Comparative Examples 12, 13, and 14 was manufactured by laminating a pressure-sensitive adhesive layer on the backing and cutting the thus obtained product into a desired size.

TABLE 4

| | Comparative Examples | | | | | |
|---|---|---|---|---|---|---|
| Constituent (part) | 9 | 10 | 11 | 12 | 13 | 14 |
| Norethisterone acetate | 5.00 | 5.0 | 5.0 | 5.0 | 5.0 | 5.0 |
| Isopropyl myristate | — | 10.00 | 10.00 | 10.00 | 10.00 | 10.00 |
| Acrylic pressure-sensitive adhesive | 94.8 | 84.80 | 84.80 | 84.80 | 84.80 | 84.80 |
| Isocyanate-based crosslinking agent | 0.2 | 0.2 | 0.2 | 0.2 | 0.2 | 0.2 |
| Backing | Thickness (μm) | | | | | |
| Polyethylene terephthalate film | 3 | 30 | 50 | — | — | — |
| Low-density polyethylene film | 50 | 50 | 50 | 50 | — | — |
| Polyvinyl chloride film | — | — | — | — | 50 | — |
| Polyurethane film | — | — | — | — | — | 50 |

Test Example 4

In Vitro Permeation Test in Rat

The abdominal region of a rat was shaved, and then the abdominal skin was extracted. The extracted skin was placed in a Franz cell, and the inside of the cell was filled with 10 mL of phosphate buffered saline (a receptor solution). In a water jacket, a hot water having a temperature of 37° C. was circulated. Each of the external patches of Examples 5, 6, and 7 and Comparative Example 9 was stamped into a circular shape (1.77 cm$^2$), and was then applied to the extracted skin of the rat. The receptor solution was sampled with the lapse of time to measure the amount of norethisterone that passed through the skin and eluted into the receptor solution according to a liquid chromatography method.

Figure 10:
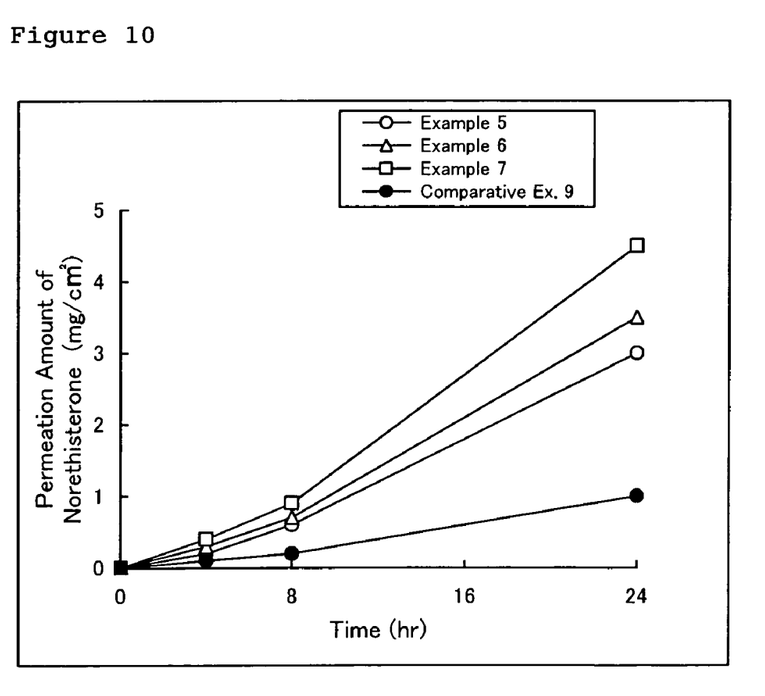
FIG. 10 is a graph, which shows the result of Test Example 4 in which an in-vitro permeation test was carried out using a rat to measure the amount of permeation.

The result is shown in FIG. 10. As is apparent from FIG. 10, in the case of the external patch of Comparative Example 9 containing no isopropyl myristate as a distribution coefficient control agent in the adhesive base material, the permeation amount of norethisterone was extremely small as compared to the cases of Examples 5, 6, and 7. From these results, it can be concluded that isopropyl myristate contained in the adhesive base material has the effect of promoting the absorption of norethisterone.

Test Example 5

Measurement of Level of Norethisterone in Blood of Rats

Four rats were used as one test group. The back region of each of the rats was shaved, and then the external patches of Example 5 and Comparative Examples 10 and 11 each having a size of 9 cm2 were applied to the back regions shaved of the rats, respectively. The blood of each of the rats was sampled with the lapse of time to measure the level of norethisterone in the blood according to a gas chromatography method. The measurement results are shown in FIG. 11.

Figure 11:
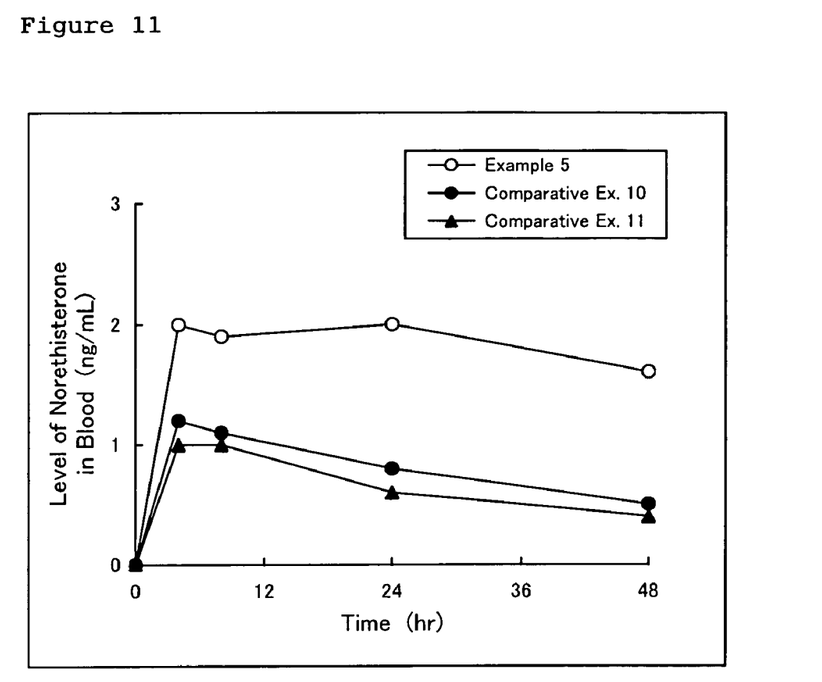
FIG. 11 is a graph, which shows the result of Test Example 5 in which the blood level of norethisterone was measured in rats.
Figure 12:
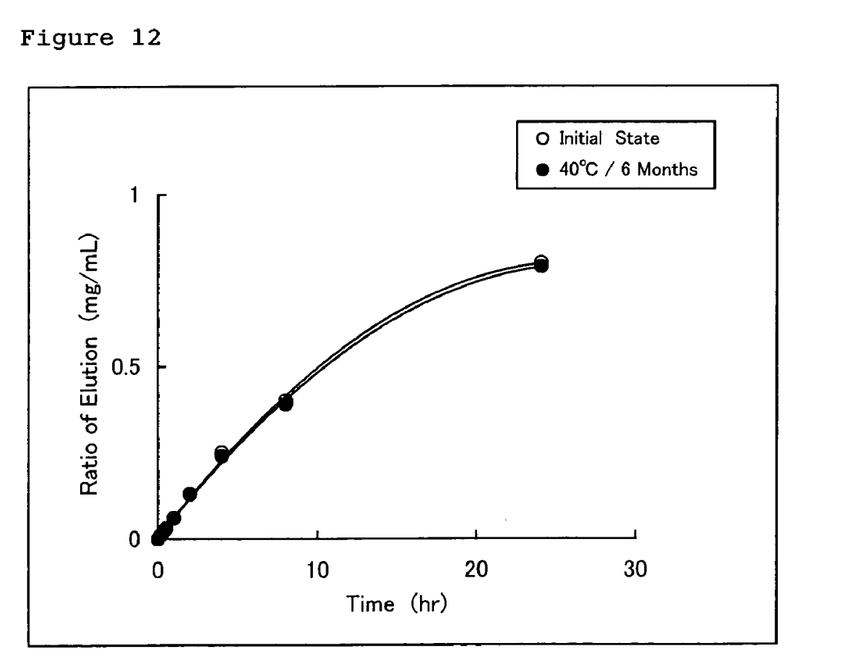
FIG. 12 is a graph, which shows the result of Test Example 6 carried out using an external patch of Example 5.
Figure 13:
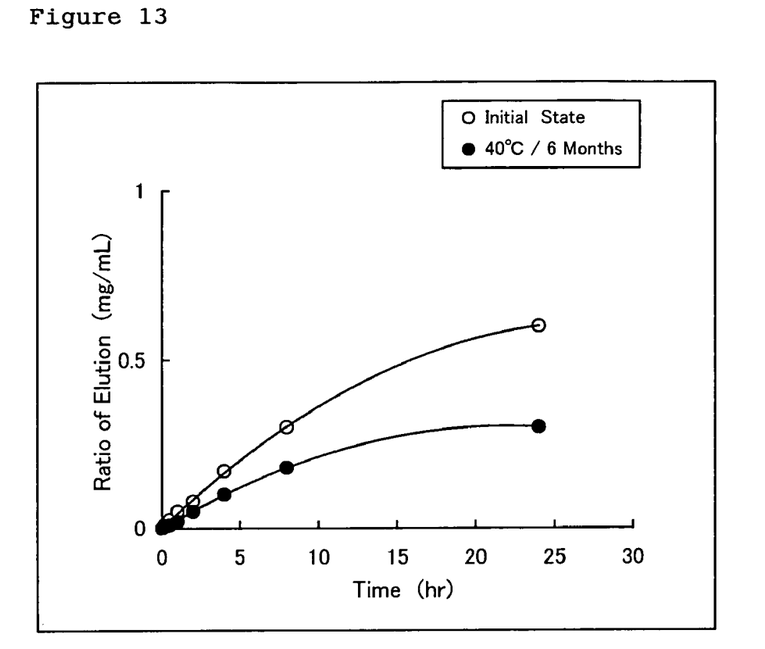
FIG. 13 is a graph, which shows the result of Test Example 6 carried out using an external patch of Comparative Example 12.
Figure 14:
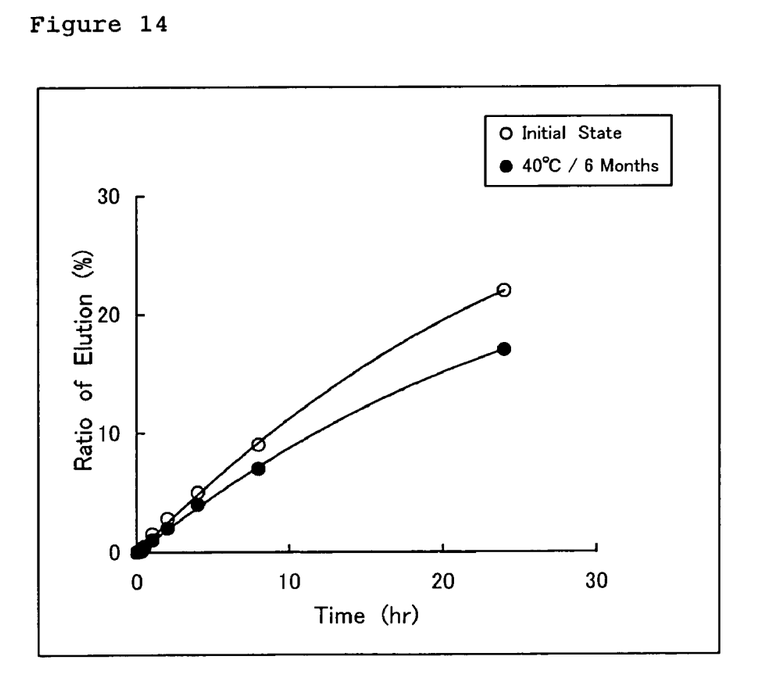
FIG. 14 is a graph, which shows the result of Test Example 6 carried out using an external patch of Comparative Example 13.
Figure 15:
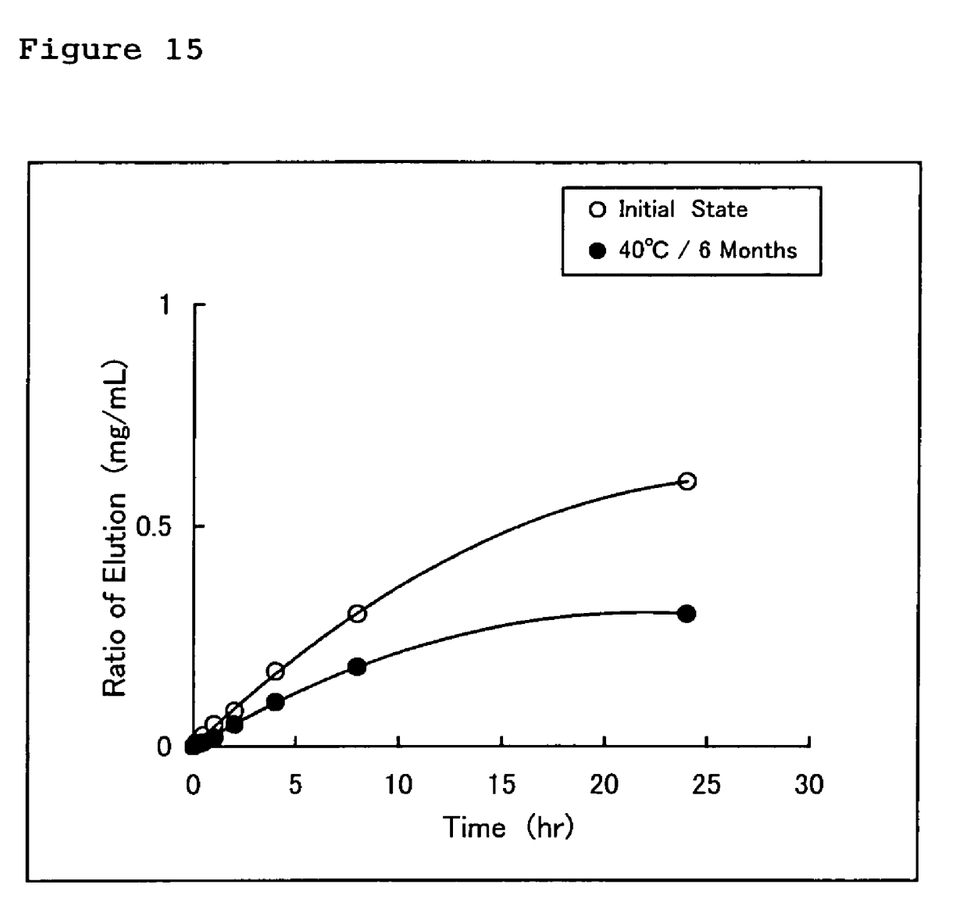
FIG. 15 is a graph, which shows the result of Test Example 6 carried out using an external patch of Comparative Example 14.

As is apparent from FIG. 11, in the case of the external patch of Example 5 manufactured using, as a backing, a laminate structure comprising a polyethylene terephthalate film having a thickness of 3 μm and a low-density polyethylene film having a thickness of 50 μm, the level of norethisterone in the blood remained at an obviously higher level by virtue of the flexibility of the backing as compared to the cases of the external patch of Comparative Example 10 manufactured using, as a backing, a laminate structure comprising a polyethylene terephthalate film having a thickness of 30 μm and a low-density polyethylene film having a thickness of 50 μm and the external patch of Comparative Example 11 manufactured using, as a backing, a laminate structure comprising a polyethylene terephthalate film having a thickness of 50 μm and a low-density polyethylene film having a thickness of 50 μm.

Test Example 6

Active Ingredient Release Test after Storage (Part 2)

The external patches of Example 5 and Comparative Examples 12, 13, and 14 were stored for 6 months at 40° C., and were then subjected to a release test according to a method shown in FIG. 4 to determine the adsorbability of norethisterone to the backing. The adsorbability of norethisterone to the backing was evaluated by comparing the releasability of norethisterone between the external patch after 6-month storage and the external patch in the initial state after manufacturing. The results are shown in FIGS. 12, 13, 14, and 15.

In each of the cases of the external patch manufactured using a low-density polyethylene film as a backing (Comparative Example 12, FIG. 13), the external patch manufactured using a polyvinyl chloride film as a backing (Comparative Example 13, FIG. 14), and the external patch manufactured using a polyurethane film as a backing (Comparative Example 14, FIG. 15), it can be concluded the releasability of norethisterone as an active ingredient was impaired due to the occurrence of adsorption of norethisterone to the backing.

On the other hand, in the case of the external patch of Example 5 manufactured using a laminate structure comprising a polyethylene terephthalate film and a low-density polyethylene film as a backing (FIG. 12), the releasability of norethisterone was not impaired even after the external patch was stored for 6 months at 40° C. From the result, it was confirmed that the adsorption of norethisterone to the backing did not occur.

INDUSTRIAL APPLICABILITY

As has been described above, the external patch according to the present invention has a pressure-sensitive adhesive layer made of an acrylic pressure-sensitive adhesive containing 0.01 to 1% by weight of an isocyanate-based crosslinking agent as an essential ingredient, and the pressure-sensitive adhesive layer contains a female hormone. In the case where the female hormone to be contained in the pressure-sensitive adhesive layer is estradiol and/or its derivative, crotamiton and oleic acid are further contained in the pressure-sensitive adhesive layer at specific ratios.

In the case where the female hormone to be contained in the pressure-sensitive adhesive layer is norethisterone and/or its derivative, isopropyl myristate is further contained in the pressure-sensitive adhesive layer at a specific ratio.

By using, as a backing, a laminate structure comprising a drug non-adsorptive layer and a flexible film for the external patch of the present invention, it becomes possible to highly dissolve a drug in the pressure-sensitive adhesive and stabilize the drug. In addition, it becomes also possible to improve the transdermal absorbability of a medical ingredient and release the drug stably for a long period of time without adsorption of the drug to the backing.

The invention claimed is:

1. An external patch comprising a backing and a pressure-sensitive adhesive layer, wherein the backing is a laminate structure comprising a flexible film as an outer layer and a drug non-adsorptive layer, wherein said flexible film has a thickness of 1 to 200 μm and is selected from at least one of the group consisting of woven fabrics, non-woven fabrics and polymer films; wherein said drug non-adsorptive layer has a thickness of 0.1 to 10 μm and is a polyethylene terephthalate film; and wherein said pressure-sensitive adhesive layer is made of an acrylic pressure-sensitive adhesive, said pressure-sensitive adhesive layer being adjacent to said drug non-adsorptive layer and not adjacent to the flexible film, wherein the adhesive layer comprises:
   0.01 to 1% by weight of an isocyanate-based crosslinking agent;
   0.5 to 10% by weight of estradiol and/or a derivative of estradiol as an active ingredient dissolved in the adhesive layer;
   0.5 to 10% by weight of crotamiton; and
   0.1 to 10% by weight of oleic acid, and
   wherein the active ingredient is not adsorbed to the backing.

2. An external patch comprising a backing and a pressure-sensitive adhesive layer, wherein the backing is a laminate structure comprising a flexible film as an outer layer and a drug non-adsorptive layer, wherein said flexible film has a thickness of 1 to 200 μm and is selected from at least one of the group consisting of woven fabrics, non-woven fabrics and polymer films; wherein said drug non-adsorptive layer has a thickness of 0.1 to 10 μm and is a polyethylene terephthalate film, said pressure-sensitive adhesive layer being adjacent to said drug non-adsorptive layer and not adjacent to the flexible film; and wherein said pressure-sensitive adhesive layer is made of an acrylic pressure-sensitive adhesive, wherein the adhesive layer comprises:
   0.01 to 1% by weight of an isocyanate-based crosslinking agent;
   1 to 30% by weight of isopropyl myristate as a distribution coefficient control agent; and
   0.5 to 10% by weight of norethisterone and/or a derivative of nonethisterone as an active ingredient, and
   wherein the active ingredient is not adsorbed to the backing.

3. An external patch comprising a backing and a pressure-sensitive adhesive layer, wherein the backing is a laminate structure comprising a low density polyethylene flexible film as an outer layer having a thickness of 1 to 200 μm and a drug non-adsorptive layer, wherein said drug non-adsorptive layer has a thickness of 0.1 to 10 μm and is a polyethylene terephthalate film; and wherein said pressure-sensitive adhesive layer is made of an acrylic pressure-sensitive adhesive, said pressure-sensitive adhesive layer being adjacent to said drug non-adsorptive layer and not adjacent to the flexible film, wherein the adhesive layer consists of:
   0.01 to 1% by weight of an isocyanate-based crosslinking agent;
   0.5 to 10% by weight of estradiol and/or a derivative of estradiol as an active ingredient;
   0.5 to 10% by weight of crotamiton; and
   0.1 to 10% by weight of oleic acid, and wherein the active ingredient is not adsorbed to the backing.

4. An external patch comprising a backing and a pressure-sensitive adhesive layer, wherein the backing is a laminate structure comprising a low density polyethylene flexible film as an outer layer having a thickness of 1 to 200 μm and a drug non-adsorptive layer, wherein said drug non-adsorptive layer has a thickness of 0.1 to 10 μm and is a polyethylene terephthalate film, and wherein said pressure-sensitive adhesive layer being adjacent to said drug non-adsorptive layer and not adjacent to the flexible film; and wherein said pressure-sensitive adhesive layer is made of an acrylic pressure-sensitive adhesive, wherein the adhesive layer consists of:
   0.01 to 1% by weight of an isocyanate-based crosslinking agent;
   1 to 30% by weight of isopropyl myristate as a distribution coefficient control agent; and 0.5 to 10% by weight of norethisterone and/or a derivative of nonethisterone as an active ingredient, and wherein the active ingredient is not adsorbed to the backing.

5. An external patch for application to a skin surface consisting of:
   a) a low density polyethylene flexible film as an outermost layer, which is oriented farthest from the skin surface when applied to the skin surface, wherein said flexible film has a thickness of 1 to 200 µm;
   b) a drug non-adsorptive as a layer adjacent to the flexible film layer, wherein said drug non-adsorptive layer has a thickness of 0.1 to 10 µm and is a polyethylene terephthalate film;
   c) a pressure-sensitive adhesive layer adjacent to the drug non-adsorptive layer and not adjacent to the flexible film, wherein the adhesive layer consists of
      0.01 to 1% by weight of an isocyanate-based crosslinking agent,
      0.5 to 10% by weight of estradiol and/or a derivative of estradiol as an active ingredient,
      0.5 to 10% by weight of crotamiton, and
      0.1 to 10% by weight of oleic acid; and
   d) a release layer adjacent to the pressure-sensitive adhesive layer and next to the skin surface when applied to the skin surface, and wherein the active ingredient is not adsorbed to the backing.

6. An external patch for application to a skin surface consisting of:
   a) a low density polyethylene flexible film as an outermost layer, which is oriented farthest from the skin surface when applied to the skin surface, wherein said flexible film has a thickness of 1 to 200 µm;
   b) a drug non-adsorptive as a layer adjacent to the flexible film layer, wherein said drug non-adsorptive layer has a thickness of 0.1 to 10 µm and is a polyethylene terephthalate film;
   c) a pressure-sensitive adhesive layer adjacent to the drug non-adsorptive layer and not adjacent to the flexible film, wherein the adhesive layer consists of
      0.01 to 1% by weight of an isocyanate-based crosslinking agent;
      1 to 30% by weight of isopropyl myristate as a distribution coefficient control agent, and
      0.5 to 10% by weight of norethisterone and/or a derivative of nonethisterone as an active ingredient; and
   d) a release layer adjacent to the pressure-sensitive adhesive layer and next to the skin surface when applied to the skin surface, and wherein the active ingredient is not adsorbed to the backing.

7. The external patch according to claim 1 or 2, wherein the flexible film is low density polyethylene film.

8. The external patch according to claim 1 or 2, wherein the acrylic component of the acrylic pressure-sensitive adhesive is selected from least one of the following compounds: 2-ethylhexyl acrylate, acrylic acid, ethyl acrylate, vinyl acetate, and an acrylic ester.

* * * * *

UNITED STATES PATENT AND TRADEMARK OFFICE
CERTIFICATE OF CORRECTION

PATENT NO. : 8,124,122 B2  
APPLICATION NO. : 10/524065  
DATED : February 28, 2012  
INVENTOR(S) : Takaya Sugawara, Sadanobu Shirai and Masahiro Yamaji Page 1 of 1

It is certified that error appears in the above-identified patent and that said Letters Patent is hereby corrected as shown below:

ON THE TITLE PAGE:

Item (73) Assignees: "Teikoku Seiyaku Co., Ltd., Osaka, Japan" should read

-- Teikoku Seiyaku Co., Ltd, Kagawa; Fuso Pharmaceutical Industries, Ltd., Osaka, both of Japan --.

Signed and Sealed this  
Twenty-ninth Day of May, 2012

David J. Kappos  
*Director of the United States Patent and Trademark Office*